United States Patent
Rottländer et al.

(10) Patent No.: US 7,342,015 B2
(45) Date of Patent: Mar. 11, 2008

(54) INDOLE DERIVATIVES

(75) Inventors: Mario Rottländer, Greve (DK); Ejner Knud Moltzen, Gentofte (DK); Ivan Mikkelsen, Koge (DK); Thomas Ruhland, Roskilde (DK); Kim Andersen, Virum (DK); Christian Krog-Jensen, Rungsted Kyst (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 358 days.

(21) Appl. No.: 10/482,762

(22) PCT Filed: Jun. 27, 2002

(86) PCT No.: PCT/DK02/00436

§ 371 (c)(1),
(2), (4) Date: Feb. 6, 2004

(87) PCT Pub. No.: WO03/002552

PCT Pub. Date: Jan. 9, 2003

(65) Prior Publication Data

US 2006/0258678 A1    Nov. 16, 2006

(30) Foreign Application Priority Data

Jun. 29, 2001   (DK) .................. 2001 01037

(51) Int. Cl.
*A61K 31/497* (2006.01)
*C07D 401/12* (2006.01)
*C07D 403/12* (2006.01)

(52) U.S. Cl. .......... 514/252.19; 514/253.09; 544/365; 544/373

(58) Field of Classification Search ........ 544/373, 544/365; 514/252.19, 253.09
See application file for complete search history.

(56) References Cited

U.S. PATENT DOCUMENTS

2003/0050307 A1*  3/2003  Ruhland et al. ............ 514/218
2004/0248883 A1   12/2004  Rottlander et al.

FOREIGN PATENT DOCUMENTS

EP   0 900 792 A1    3/1999
WO   WO-99/55672 A2  11/1999

OTHER PUBLICATIONS

Jones et al. Pharmacology, Biochemistry and Behavior, vol. 71, p. 555-568 (2002).*
TenBrink et al. J. Med. Chem. vol. 39, p. 2435-2437 (1996).*
Robichaud et al. Annual Reports in Medicinal Chemistry, vol. 36, p. 11-20 (2000).*
U.S. Appl. No. 11/758,511, filed Jun. 5, 2007, Rottlander, et al.

* cited by examiner

Primary Examiner—James O. Wilson
Assistant Examiner—Ebenezer Sackey
(74) Attorney, Agent, or Firm—Stephen G. Kalinchak

(57) ABSTRACT

A heteroaryl derivative having the formula (I). The compounds of the invention are considered useful for the treatment of affective disorders such as general anxiety disorder, panic disorder, obsessive compulsive disorder, depression, social phobia and eating disorders, and neurological disorders such as psychosis (I)

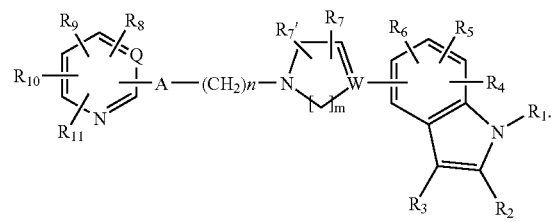

17 Claims, No Drawings

INDOLE DERIVATIVES

The present invention relates to novel heteroaryl derivatives potently binding to the 5-HT$_{1A}$ receptor, pharmaceutical compositions containing these compounds and the use thereof for the treatment of certain psychiatric and neurological disorders. Many of the compounds of the invention have also potent serotonin reuptake inhibition activity and are thus considered particularly useful for the treatment of depression.

Furthermore, many compounds of the invention have also effect at dopamine D$_3$ and D$_4$ receptors and are considered to be useful for the treatment of psychosis.

BACKGROUND ART

Clinical and pharmacological studies have shown that 5-HT$_{1A}$ agonists and partial agonists are useful in the treatment of a range of affective disorders such as generalised anxiety disorder, panic disorder, obsessive compulsive disorder, depression and aggression.

It has also been reported that 5-HT$_{1A}$ ligands may be useful in the treatment of ischaemia.

An overview of 5-HT$_{1A}$ antagonists and proposed potential therapeutic targets for these antagonists based upon preclinical and clinical data are presented by Schechter et al. *Serotonin* 1997, Vol. 2, Issue 7. It is stated that 5-HT$_{1A}$ antagonists may be useful in the treatment of schizophrenia, senile dementia, dementia associated with Alzheimer's disease, and in combination with SSRI antidepressants also to be useful in the treatment of depression.

5-HT reuptake inhibitors are well-known antidepressant drugs and useful for the treatment of panic disorders and social phobia.

The effect of combined administration of a compound that inhibits serotonin reuptake and a 5-HT$_{1A}$ receptor antagonist has been evaluated in several studies mis, R. B. et al. *Eur., J. Pharmacol.* 1987, 143, p 195-204 and Gartside, S. E. *Br. J. Pharmacol.* 1995, 115, p 1064-1070, Blier, P. et al. *Trends Pharmacol. Sci.* 1994, 15, 220). In these studies it was found that combined 5-HT$_{1A}$ receptor antagonists and serotonin reuptake inhibitors would produce a more rapid onset of therapeutic action.

Dopamine D$_4$ receptors belong to the family of dopamine D$_2$-like receptors which is considered to be responsible for the antipsychotic effects of neuroleptics. Dopamine D$_4$ receptors are primarily located in areas of the brain other than striatum, suggesting that dopamine D$_4$ receptor ligands have antipsychotic effect and are devoid of extrapyramidal activity.

Accordingly, dopamine D$_4$ receptor ligands are potential drugs for the treatment of psychosis and positive symptoms of schizophrenia and compounds with combined effects at dopamine D$_4$, and serotonergic receptors may have the further benefit of improved effect on negative symptoms of schizophrenia, such as anxiety and depression, alcohol abuse, impulse control disorders, aggression, side effects induced by conventional antipsychotic agents, ischaemic disease states, migraine, senile dementia and cardiovascular disorders and in the improvement of sleep.

Dopamine D$_3$ receptors also belong to the family of dopamine D$_2$-like receptors. D$_3$ antagonistic properties of an antipsychotic drug could reduce the negative symptoms and cognitive deficits and result in an improved side effect profile with respect to EPS and hormonal changes.

Accordingly, agents acting on the 5-HT$_{1A}$ receptor, both agonists and antagonists, are believed to be of potential use in the therapy of psychiatric and neurological disorders and thus being highly desired. Furthermore, antagonists, at the same time having potent serotonin reuptake inhibition activity and/or D$_4$ and/or D$_3$ activity, may be particularly useful for the treatment of various psychiatric and neurological diseases.

Previously, closely related structures have been reported:
WO 9955672 discloses a general formula in which indole derivatives having 5-HT$_{1A}$ receptor and D$_2$ receptor affinity are included
EP 900792 discloses a general formula in which indole derivatives are embraced as 5-HT$_{1A}$ and 5-HT$_{1D}$ as well as D$_2$ receptor ligands.

It has now been found that a class of indole derivatives is particularly useful as 5-HT$_{1A}$ ligands. Furthermore, it has been found that many of these compounds have other highly beneficial properties as e.g. potent serotonin reuptake inhibition activity and/or affinity for the D$_4$ receptor.

SUMMARY OF THE INVENTION

The invention comprises the following:
A compound represented by the general formula I

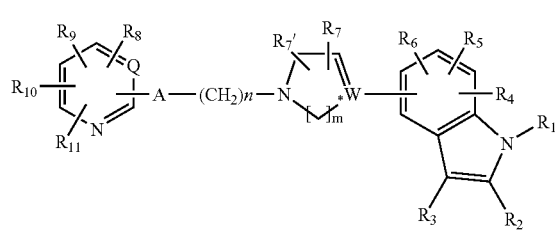

wherein
A represents O or S;
n is 2, 3, 4, 5, 6, 7, 8, 9 or 10;
m is 2 or 3;
W represents N, C or CH;
Q represents N, C or CH;
and the dotted line represents an optional bond;
R$^1$ represents hydrogen, C$_{1-6}$-alkyl, C$_{2-6}$-alkenyl, C$_{2-6}$-alkynyl, C$_{3-8}$-cycloalkyl-C$_{1-6}$-alkyl, aryl-C$_{1-6}$-alkyl or acyl;
R$^2$, R$^3$, R$^4$, R$^5$ and R$^6$ independently represent hydrogen, halogen, cyano, nitro, C$_{1-6}$-alkyl, C$_{1-6}$alkoxy, C$_{1-6}$-alkylsulfanyl, C$_{1-6}$ alkylsulfonyl, hydroxy, hydroxy-C$_{1-6}$-alkyl, C$_{1-6}$-alkoxycarbonyl, acyl, C$_{3-8}$-cycloalkyl, C$_{3-8}$-cycloalkyl-C$_{1-4}$-alkyl, trifluoromethyl, trifluoromethoxy, NR$^{15}$R$^{16}$ wherein R$^{15}$ and R$^{16}$ independently represent hydrogen, C$_{1-6}$-alkyl, C$_{3-8}$-cycloalkyl or phenyl; or R$^{15}$ and R$^{16}$ together with the nitrogen to which they are attached form a 5- or 6-membered ring optionally containing one further heteroatom;
R$^7$ and R$^{7'}$ independently represent hydrogen or C$_{1-6}$-alkyl or may together form a bridge consisting of two or three methylene groups;
R$^8$, R$^9$, R$^{10}$ and R$^{11}$ are each independently selected from hydrogen, halogen, nitro, cyano, trifluoromethyl, trifluoromethoxy, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, phenyl, thiophenyl, C$_{1-6}$-alkoxy, C$_{1-6}$-alkylsulfanyl, C$_{1-6}$-alkylsulfonyl, hydroxy, formyl, acyl, acylamino, aminocarbonyl, C$_{1-6}$-alkoxycarbonylamino, aminocarbonylamino, C$_{1-6}$-alkylaminocarbonylamino and di(C$_{1-6}$-alkyl)aminocarbonylamino, $NR^{13}R^{14}$ wherein $R^{13}$ and $R^{14}$ independently represent hydrogen, $C_{1-6}$-alkyl, $C_{3-8}$-cycloalkyl or phenyl; or $R^{13}$ and $R^{14}$ together with the nitrogen to which they are attached form a 5- or 6-membered carbocyclic ring optionally containing one further heteroatom;

its enantiomers, and a pharmaceutically acceptable acid addition salt thereof.

The invention also relates to a pharmaceutical composition comprising a compound of formula (I) or a pharmaceutically acceptable salt thereof and at least one pharmaceutically acceptable carrier or diluent.

In a further embodiment, the invention relates to the use of a compound of formula (I) or a pharmaceutically acceptable acid addition salt thereof for the preparation of a medicament for the treatment of a disorder or disease responsive to the inhibition of serotonin uptake and antagonism of 5-$HT_{1A}$ receptors.

In a further embodiment, the invention relates to the use of a compound of formula (I) or a pharmaceutically acceptable acid addition salt thereof for the preparation of a medicament for the treatment of a disorder or disease responsive to the combined effect of 5-$HT_{1A}$ receptors and dopamine $D_4$ receptors.

In particular, the invention relates to the use of a compound according to the invention or a pharmaceutically acceptable acid addition salt thereof for the preparation of a medicament for the treatment of affective disorders such as general anxiety disorder, panic disorder, obsessive compulsive disorder, depression, social phobia and eating disorders; other psychiatric disorders such as psychosis and neurological disorders.

In still another embodiment, the present invention relates to a method for the treatment of a disorder or disease of living animal body, including a human, which is responsive to the inhibition of serotonin uptake and antagonism of 5-$HT_{1A}$ receptors comprising administering to such a living animal body, including a human, a therapeutically effective amount of a compound of formula (I) or a pharmaceutically acceptable acid addition salt thereof.

In still another embodiment, the present invention relates to a method for the treatment of a disorder or disease of living animal body, including a human, which is responsive to the effect of 5-$HT_{1A}$ and $D_4$ receptors comprising administering to such a living animal body, including a human, a therapeutically effective amount of a compound of formula (I) or a pharmaceutically acceptable acid addition salt thereof.

Due to their combined antagonism of 5-$HT_{1A}$ receptors and serotonin reuptake inhibiting effect, the compounds of the invention are considered particularly useful as fast onset of action medicaments for the treatment of depression. The compounds may also be useful for the treatment of depression in patients who are resistant to treatment with currently available antidepressants.

The compounds of the invention have high affinity for the 5-$HT_{1A}$ and $D_4$ receptors. Accordingly, the compounds of the invention are considered useful for the treatment of affective disorders such as general anxiety disorder, panic disorder, obsessive compulsive disorder, depression, social phobia and eating disorders; other psychiatric disorders such as psychosis and neurological disorders.

DETAILED DESCRIPTION OF THE INVENTION

In preferred embodiments of the invention, n is 2, 3 or 4

In preferred embodiments of the invention, W represents N;

In preferred embodiments of the invention, Q represents N;

In preferred embodiments of the invention, Q represents C or CH;

In preferred embodiments of the invention, $R^7$ and $R^{7'}$ are both hydrogen;

In preferred embodiments of the invention, $R^1$ is hydrogen;

In preferred embodiments of the invention, $R^2$, $R^3$, $R^4$, $R^5$ and $R^6$ represent hydrogen;

In preferred embodiments of the invention, $R^8$, $R^9$, $R^{10}$ and $R^{11}$ independently represent hydrogen, halogen, $C_{1-6}$-alkyl, $C_{3-8}$-cycloalkyl, CN, $CF_3$, $OCF_3$, $NH_2$, $NR^{13}R^{14}$ wherein $R^{13}$ and $R^{14}$ independently represent hydrogen, $C_{1-6}$-alkyl, $C_{3-8}$-cycloalkyl or phenyl; or $R^{13}$ and $R^{14}$ together with the nitrogen form a piperidine or pyrrolidine;

In more preferred embodiments of the invention, $R^8$, $R^9$, $R^{10}$, $R^{11}$ and $R^{12}$ independently represent methyl, cyclopropyl, trifluoromethyl, cyano, chloro, bromo, piperidinyl, phenyl;

In a preferred embodiment of the invention, the compounds of formula I as described above are:

2-{2-[4-(1H-Indol-4-yl)piperazin-1-yl]ethylsulfanyl}-4,6-dimethylnicotinonitrile, 1a 2-{2-[4-(1H-Indol-4-yl)piperazin-1-yl]ethylsulfanyl}-6-(thiophen-2-yl)-4-trifluoromethylnicotinonitrile, 1b 2-{2-[4-(1H-Indol-4-yl)piperazin-1-yl] ethylsulfanyl}pyridine, 1c 2-{2-[4-(1H-Indol-4-yl)piperazin-1-yl]ethylsulfanyl}-6-methylnicotinonitrile, 1d 3-{2-[4-(1H-Indol-4-yl)piperazin-1-yl]ethoxy}-2-chloropyridine, 1e 3-{2-[4-(1H-Indol-4-yl)piperazin-1-yl]ethoxy}-2-bromopyridine, 1f 3-{2-[4-(1H-Indol-4-yl)piperazin-1-yl]ethoxy}-2-methylpyridine, 1g 3-{2-[4-(1H-Indol-4-yl)piperazin-1-yl]ethoxy}-5-chloropyridine, 1h 2-{4-[4-(1H-Indol-4-yl)piperazin-1-yl]butylsulfanyl}-5-trifluoromethylpyridine, 1i 2-{4-[4-(1H-Indol-4-yl)piperazin-1-yl]butylsulfanyl}-4,6-dimethylnicotinonitrile, 1j 2-{3-[4-(1H-Indol-4-yl)piperazin-1-yl]propylsulfanyl}-5-trifluoromethylpyridine, 1k 2-{3-[4-(1H-Indol-4-yl)piperazin-1-yl]propylsulfanyl}-4,6-dimethylnicotinonitrile, 1l 2-{2-[4-(1H-Indol-4-yl)piperazin-1-yl]ethylsulfanyl}-6-methylnicotinamide, 2a 2-{2-[4-(1H-Indol-4-yl)piperazin-1-yl] ethylsulfanyl}nicotinonitrile, 2b 2-{2-[4-(1H-Indol-4-yl)piperazin-1-yl]ethylsulfanyl}-4-methylpyridine, 2c 2-{2-[4-(1H-Indol-4-yl)piperazin-1-yl]ethylsulfanyl}-4-methyl-6-(piperidin-1-yl)nicotinonitrile, 2d 2-{2-[4-(1H-Indol-4-yl)piperazin-1-yl]ethylsulfanyl}-4-trifluoromethyl-6-cyclopropylnicotinonitrile, 2e 2-{2-[4-(1H-Indol-4-yl)piperazin-1-yl]ethylsulfanyl}-3-methanesulfonyl-4-methyl-6-phenylpyridine, 2f 2-{2-[4-(1H-Indol-4-yl)piperazin-1-yl] ethoxy}nicotinonitrile, 2g 2-{2-[4-(1H-Indol-4-yl)piperazin-1-yl]ethoxy}-4-methylpyridine, 2h
2-{2-[4-(1H-Indol-4-yl)piperazin-1-yl]ethoxy}-6-methylnicotinamide, 2i
2-{2-[4-(1H-Indol-4-yl)piperazin-1-yl]ethoxy}-4-methyl-6-(piperidin-1-yl)nicotinonitrile, 2j
2-{2-[4-(1H-Indol-4-yl)piperazin-1-yl]ethoxy}-4-trifluoromethyl-6-cyclopropylnicotinonitrile, 2k
2-{2-[4-(1H-Indol-4-yl)piperazin-1-yl]ethoxy}-3-methanesulfonyl-4-methyl-6-phenylpyridine, 2l
6-Chloro-2-{2-[4-(1H-indol-4-yl)piperazin-1-yl]ethylsulfanyl}-4-methylnicotinonitrile, 2m
6-Chloro-5-fluoro-2-{2-[4-(1H-indol-4-yl)piperazin-1-yl]ethylsulfanyl}nicotinonitrile, 2n
4,6-Dimethyl-2-{2-[4-(1H-indol-4-yl)piperazin-1-yl]ethylsulfanyl}pyrimidine, 2o
5-Cyano-4-{2-[4-(1H-indol-4-yl)piperazin-1-yl]ethylsulfanyl}pyrimidine, 2p
5-Cyano-4-{2-[4-(1H-indol-4-yl)piperazin-1-yl]ethylsulfanyl}-6-methylsulfanyl-2-phenylpyrimidine, 2q
5-Ethyl-2-{2-[4-(1H-indol-4-yl)piperazin-1-yl]ethylsulfanyl}pyrimidine, 2r
2-{2-[4-(1H-Indol-4-yl)piperazin-1-yl]ethylsulfanyl}-4-trifluoromethylpyrimidine, 2s or a pharmaceutical acceptable salt thereof.

Definition of Substituents etc.

The term $C_{1-6}$ alkyl refers to a branched or linear alkyl group having from one to six carbon atoms inclusive, including, but not limited to, methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms inclusive wherein the groups are having at least one double bond or triple bond, respectively.

The terms $C_{1-6}$-alkoxy, $C_{1-6}$ alkylsulfanyl, $C_{1-6}$ alkylsulfonyl, $C_{1-6}$ alkylamino, $C_{1-6}$ alkylcarbonyl, hydroxy-$C_{1-6}$-alkyl etc. designate such groups in which the $C_{1-6}$ alkyl is as defined above.

The term $C_{3-8}$ cycloalkyl designates a monocyclic or bicyclic carbocycle having three to eight C-atoms, including, but not limited to, cyclopropyl, cyclobutyl, cyclopentyl, cyclohexyl, etc.

The term aryl refers to a carbocyclic aromatic group, such as phenyl, naphthyl, in particular phenyl. As used herein, aryl may be substituted one or more times with halogen, nitro, cyano, trifluoromethyl, $C_{1-6}$-alkyl, hydroxy and $C_{1-6}$-alkoxy.

Halogen means fluoro, chloro, bromo or iodo.

As used herein, the term acyl refers to formyl, $C_{1-6}$-alkylcarbonyl, arylcarbonyl, aryl-$C_{1-6}$-alkylcarbonyl wherein the aryl is as defined above, $C_{3-8}$-cycloalkylcarbonyl or a $C_{3-8}$-cycloalkyl-$C_{1-6}$alkyl-carbonyl group.

The term aminocarbonyl means —CO-amino wherein amino is defined as above.

The term acylamino means a group of the formula —NH-COH, —NHCO—$C_{1-6}$-alkyl, —NHCO-aryl, —NHCO—$C_{3-8}$-cycloalkyl, —NHCO—$C_{3-8}$-cycloalkyl-$C_{1-6}$-alkyl, wherein the alkyl, cycloalkyl and aryl are as defined above.

The terms aminocarbonylamino, $C_{1-6}$-alkylaminocarbonylamino and di($C_{1-6}$-alkyl)aminocarbonylamino mean a group of the formula NHCONH$_2$, —NHCONHC$_{1-6}$-alkyl, NHCON(di-$C_{1-6}$-alkyl), respectively.

The acid addition salts of the invention are preferably pharmaceutically acceptable salts of the compounds of the invention formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (e.g. enantiomers). The invention includes all such isomers and any mixtures thereof including racemic mixtures.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization of d- or l-(tartrates, mandelates or camphorsulphonate) salts for example. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981).

Optically active compounds can also be prepared from optically active starting materials.

Finally, formula (I) includes any tautomeric forms of the compounds of the invention.

The compounds of the invention can be prepared by one of the following methods comprising:

a) treating a compound of formula (II) with a compound of formula (I in the presence of a reducing agent.

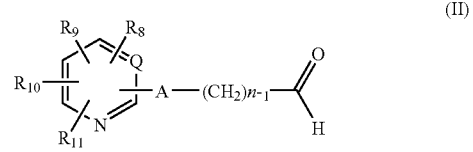

(II)

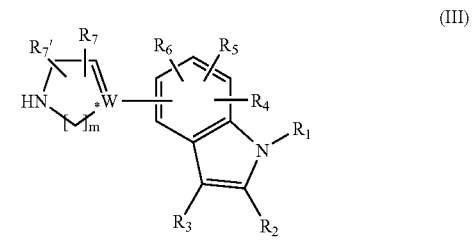

(III)

wherein n, m, $R^1$-$R^{11}$, Q, W, A and the dotted line are as defined above;

b) treating a compound of formula (IV) with a compound of formula (V) in the presence of an appropriate base

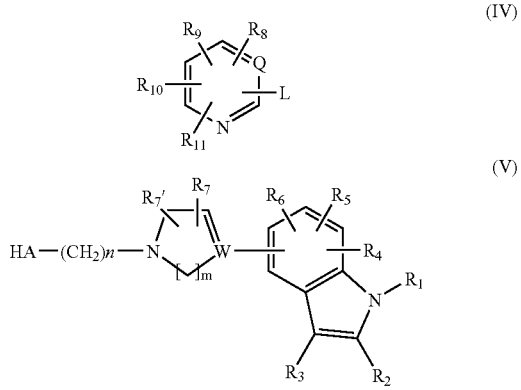

wherein L is a suitable leaving group such as e.g. chloro and n, m, $R^1$-$R^{12}$, Q, W, A and the dotted line are as defined above.

The compounds of formula (I) are isolated as the free base or in the form of a pharmaceutically acceptable salt thereof.

The reductive amination according to method a) is preferably carried out in an inert organic solvent such as dimethylformamide or tetrahydrofuran in the presence of a reducing agent, e.g. triacetoxyborohydride, at room temperature.

The arylation according to method b) is conveniently performed in an inert organic solvent such as dimethylformamide in the presence of a base (e.g. potassium tert-butoxide) at a temperature in the range of 40-100° C., preferably in the range of 40-80° C. and most preferred around 50° C.

Preparation of indolyl piperazines and tetrahydropyridyl piperazines of formula (III) is described in WO 9967237. Aldehydes of formula (II) are prepared as described in the Examples below. Alcohols and mercaptans of formula (V) are prepared as described in the Examples below. The starting chloropyridines of formula (IV) are commercially available or made by methods well-described in the literature The following examples will illustrate the invention further. They are, however, not to be construed as limiting.

EXAMPLES

Melting points were determined on a Btichi SMP-20 apparatus and are uncorrected. Analytical LC-MS data were obtained on a PE Sciex API 150EX instrument equipped with IonSpray source (method D) or heated nebulizer (APCI, methods A and B) and Shimadzu LC-8A/SLC-10A LC system. The LC conditions [30×4.6 mm YMC ODS-A with 3.5 µm particle size] were linear gradient elution with water/acetonitrile/trifluoroacetic acid (90:10:0.05) to water/acetonitrile/trifluoroacetic acid (10:90:0.03) in 4 min at 2 mL/min. Purity was determined by integration of the UV trace (254 nm). The retention times $R_t$ are expressed in minutes.

Mass spectra were obtained by an alternating scan method to give molecular weight information. The molecular ion, MH+, was obtained at low orifice voltage (5-20V) and fragmentation at high orifice voltage (100V).

Preparative LC-MS-separation was performed on the same instrument. The LC conditions (50×20 mm YMC ODS-A with 5 µm particle size) were linear gradient elution with water/acetonitrile/trifluoroacetic acid (80:20:0.05) to water/acetonitrile/trifluoroacetic acid (10:90:0.03) in 7 min at 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated chloroform (99.8% D) or dimethyl sulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, t=triplet of triplets, m=multiplet, b=broad singlet. NMR signals corresponding to acidic protons are generally omitted. Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography silica gel of type Kieselgel 60, 230-400 mesh ASTM was used. For ion-exchange chromatography (SCX, 1 g, Varian Mega Bond Elut®, Chrompack cat. no. 220776). Prior use the SCX-columns were pre-conditioned with 10% solution of acetic acid in methanol (3 mL).

Example 1

4,6-Dimethyl-2-(2-oxo-ethylsulfanyl)-nicotinonitrile 4,6-Dimethyl-2-mercaptonicotinonitrile (3.0 g) was dissolved in DMF (40 mL) and a solution of potassium tert-butoxide (19.2 mL; 1 M) in tert-butanol added. The mixture was stirred for 10 min, added dropwise to a solution of bromoacetaldehyd-dimethylacetal (3.2 g) in DMF (10 mL) and stirred over night at 70° C. The mixture was poured on water and extracted with ethyl acetate, the combined organic phases dried and evaporated to give an oil (5.3 g) which was dissolved in dioxane (40 mL), HCl (20 mL; 3 M) was added and the mixture was stirred at 30° C. for 2 h. $NaHCO_3$ was added until pH reached 5-6, the mixture was extracted with ethyl acetate, the combined organic phases dried with $Na_2SO_4$ and evaporated to give the title compound as an oil (2.9 g). $^1$H NMR (CDCl$_3$): δ 2.45 (s, 6H); 3.35 (d, 2H); 6.85 (s, 1H); 9.55 (t, 1H).

2-{2-[4-(1H-Indol-4-yl-piperazin-1-yl]ethylsuofanyl}-4,6-dimethylnicotinonitrile 1a 4,6-Dimethyl-2-(2-oxo-ethylsulfanyl)nicotinonitrile (2.9 g) was dissolved in 1,2-dichloroethane (150 mL), a solution of 1-(1H-indol-4-yl)piperazine (2.4 g) in DMF (150 mL) was added, sodium triacetoxyborohydride (14.9 g) was then added followed by stirring for 2 h. The mixture was poured on water and $Na_2CO_3$ added until pH reached 7-8. The mixture was extracted with ethyl acetate, the combined organic phases dried and evaporated to give an oil which was subjected to purification by column chromatography (silica gel; ethyl acetate and heptane) giving an oil which precipitated as the oxalate salt (0.36 g) from acetone. LC/MS (m/z) 392 (MH+), RT=1.92, purity: 99%.

In a similar manner the following compounds were prepared:
2-{2-[4(1H-Indol-4-yl)piperazin-1-yl]ethylsuyanyl}-6-(thiophen-2-yl)-4-trifluoromethylinicotinonitrile, 1b: LC/MS (m/z) 514 (MH+), RT=2.54, purity: 100%.

2-{2-[4-(1H-Indol-4-yl)piperazin-1-yl]ethylsulfanyl}ypyridine, 1c: LC/S (m/z) 339 (MH+), RT=1.58, purity: 83%.

2-{2-[4-(1H-Indol-4-yl)piperazin-1-yl]ethylsulfanyl}-6-methylnicotinonitrile, 1d: LC/MS (m/z) 378 (MH+), RT=1.95, purity: 92%.

3-{2-[4-(1H-Indol-4-yl)piperazin-1-yl]ethoxy}-2-chloropyridine, 1e: LC/MS (m/z) 357 (MH+), RT=1.50, purity: 93%.

3-{2-[4-(1H-Indol-4-yl)piperazin-1-yl]ethoxy}-2-bromopyridine, 1f: LC/MS (m/z) 403 (MH+), RT=1.54, purity: 89%.

3-{2-[4-(1H-Indol-4-yl)piperazin-1-yl]ethoxy}-2-methylpyridine, 1g: LC/MS (m/z) 337 (MH+), RT=0.71, purity: 78%.

3-{2-[4-(1H-Indol-4-yl)piperazin-1-yl]ethoxy}-5-chloropyridine, 1h: LC/MS (m/z) 357 (MH+), RT=1.58, purity: 100%.

2-{4-[4-(1H-Indol-4-yl)piperazin-1-yl]butylsulfanyl}-5-trifluoromethylpyridine, 1i: LC/MS (m/z) 435 (MH+), RT=2.14, purity: 80%.

2-{4-[4-(1H-Indol-4-yl)piperazin-1-yl]butylsulfanyl}-4,6-dimethylnicotinonitrile, 1j: LC/MS (m/z) 420 (MH+), RT=2.07, purity: 75%.

2-{3-[4-(1H-Indol-4-yl)piperazin-1-yl]propylsulfanyl}-5-trifluoromethylpyridine, 1k: LC/MS (m/z) 421 (MH+), RT=2.06, purity: 98%.

2-{3-[4-(1H-Indol-4-yl)piperazin-1-yl]propylsulfanyl}-4,6-dimethylnicotitionitrile, 1l: LC/MS (m/z) 406 (MH+), RT=1.99, purity: 100%.

Example 2

2-[4-(1H-Indol-4-yl)-piperazin-1-yl]-ethanethiol 1-(1H-Indol-4-yl)piperazine (3.9 g) and thiirane (1.75 g) was dissolved in DMF (200 mL) and refluxed for 1 h. The mixture was evaporated and re-dissolved in TBF, dried with MgSO$_4$, filtered and evaporated to give the an oil which was subjected to purification by column chromatography (silica gel; ethyl acetate and heptane) giving the title compound as an oil (2,2 g). MS m/z (%): 261 (MH+, 100%), 202 (100%), 159 (23%).

2-{2-[4(1H-Indol-4-yl)piperazin-1-yl-ethylsulfanyl}-6-methylnicotinonitrile, 2a

2-[4-(1H-Indol-4-yl)piperazin-1-yl]ethanethiol (2.2 g) was dissolved in a solution of potassium tert-butoxide (0.81 g) in DMF (25 mL), stirred for 15 min and heated to 50° C. A solution of 6-methyl-2-chloronicotinonitrile (1.91 g) in DMF (25 mL) was added drop wise and stirring was continued for another 2 h at 50° C. The mixture was evaporated and re-dissolved in THF, washed with brine, dried with MgSO$_4$, filtered and evaporated to give an oil which was subjected to purification by column chromatography (silica gel; ethyl acetate, heptane and triethyl amine) giving the title compound as an oil which precipitated as the oxalate salt from acetone. LC/MS (m/z) 396 (MH+), RT=1.46, purity: 91%.

In a similar manner the following compounds were prepared:

2-{2-[4-(1H-Indol-4-yl)piperazin-1-yl]ethylsulfanyl}nicotinonitrile, 2b: LC/MS (m/z) 364 (MH+), RT=1.66, purity: 96%.

2-{2-[4-(1H-Indol-4-yl)piperazin-1-yl]ethylsulfanyl}-4-methylpyridine, 2c: LC/MS (m/z) 353 M+), RT=1.70, purity: 87%.

2-{2-[4-(1H-Indol-4-yl)piperazin-1-yl]ethylsulfanyl}-4-methyl-6-(piperidin-1-yl)nicotinonitrile, 2d: LC/MS (m/z) 461 (MH+), RT=2.29, purity: 95%.

2-{2-[4-(1H-Indol-4-yl)piperazin-1-yl]ethylsulfanyl}-4-trifluoromethyl-6-cyclopropylnicotinonitrile, 2e: LC/MS (m/z) 472 (MH+), RT=2.33, purity: 94%.

2-{2-[4-(1H-Indol-4-yl)piperazin-1-yl]ethylsulfanyl}-3-methanesulfonyl-4-methyl-6-phenylpyridine, 2f: LC/MS (m/z) 507 (MH+), RT=2.16, purity: 92%.

2-{2-[4-(1H-Indol-4-yl)piperazin-1-yl]ethoxy}nicotinonitrile, 2g: LC/MS (m/z) 348 (MH+), RT=1.46, purity: 88%.

2-{2-[4-(1H-Indol-4-yl)piperazin-1-yl]ethoxy}-4-methylpyridine, 2h: LC/MS (m/z) 337 (MH+), RT=1.66, purity: 100%.

2-{2-[4-(1H-Indol-4-yl)piperazin-1-yl]ethoxy}-6-methylnicotinamide, 2i: LC/MS (m/z) 380 (MH+), RT=1.41, purity: 96%.

2-{2-[4-(1H-Indol-4-yl)piperazin-1-yl]ethoxy}-4-methyl-6-(piperidin-1-yl)nicotinonitrile, 2j: LC/MS (m/z) 445 (MH+), RT=2.24, purity: 100%.

2-{2-[4-(1H-Indol-4-yl)piperazin-1-yl]ethoxy}-4-trifluoromethyl-6-cyclopropylnicotinonitrile, 2k: LC/MS (m/z) 456 (MH+), RT=2.20, purity: 100%.

2-{2-[4-(1H-Indol-4-yl)piperazin-1-yl]ethoxy}-3-methanesulfonyl-4-methyl-6-phenylpyridine, 2l: LC/MS (m/z) 491 (MH+), RT=2.16, purity: 70%.

6-Chloro-2-{2-[4-(1H-indol-4-yl)piperazin-1-yl]ethylsulfanyl}-4-methylnicotinonitrle, 2m: LC/MS (m/z) 413 (H+), RT=2.00, purity: 69%.

6-Chloro-n-fluoro-2-{2-[4-(1H-indol-4-yl)piperazin-1-yl]ethylsulfanyl}nicotinonitrile, 2n: LC/MS (m/z) 417 (M+), RT=1.91, purity: 85%.

2-{2-[4-(1H-Indol-4-yl)piperazin-1-yl]ethylsulfanyl}pyrimidine, 2o: LC/MS (m/z) 368 (MH+), RT=1.62, purity: 73%.

5-Cyano-4-{2-[4-(1H-indol-4-yl)piperazin-1-yl]ethylsulfanyl}pyrimidine, 2p: LC/MS (m/z) 365 (MH+), RT=1.62, purity: 90%.

5-Cyano-4-{2-[4-(1H-indol-4-yl)piperazin-1-yl]ethylsuyfanyl}-6-methylsulfanyl-2-phenylpyrimidine, 2q: LC/MS (m/z) 488 (MH+), RT=2.49, purity: 93%.

5-Ethyl-2-{2-[4-(1H-indol-4-yl)piperazin-1-yl]ethylsulfanyl}pyrimidine, 2r: LC/MS (m/z) 368 (MH+), RT=1.79, purity: 72%.

2-{2-[4-(2H-Indol-4-yl)piperazin-1-yl]ethylsulfanyl}-4-trifluoromethylpyrimidine, 2s: LC/MS (m/z) 408 (MH+), RT=1.91, purity: 79%.

Pharmacological Testing

The affinity of the compounds of the invention to 5-HT$_{1A}$ receptors was determined by measuring the inhibition of binding of a radioactive ligand at 5-HT$_{1A}$ receptors as described in the following test:

Inhibition of $^3$H-5-CT Binding to Human 5-HT$_{1A}$ Receptors.

By this method, the inhibition by drugs of the binding of the 5-HT$_{1A}$ agonist $^3$H-5-carboxamido tryptamine (3H-5-CT) to cloned human 5-HT$_{1A}$ receptors stably expressed in transfected HeLa cells (HA7) (Fargin, A. et al. *J. Biol. Chem.* 1989, 264, 14848) is determined in vitro. The assay was performed as a modification of the method described by Harrington, M. A. et al. *J. Pharmacol. Exp. Ther.* 1994, 268, 1098. Human 5-HT$_{1A}$ receptors (40 µg of cell homogenate) were incubated for 15 minutes at 37° C. in 50 mM Tris buffer at pH 7.7 in the presence of $^3$H-5-CT. Non-specific binding was determined by including 10 µM of metergoline. The reaction was terminated by rapid filtration through Unifilter GF/B filters on a Tomtec Cell Harvester. Filters were counted in a Packard Top Counter. Compounds 1d, 2b, 2e and 2o were tested and showed IC$_{50}$ values of less than 50 nM.

The compounds of the invention have also been tested for their effect on re-uptake of serotonin in the following test:

Inhibition of $^3$H-5-HT Uptake Into Rat Brain Synaptosomes.

Using this method, the ability of drugs to inhibit the accumulation of $^3$H-5-HT into whole rat brain synaptosomes is determined in vitro. The assay was performed as described by Hyttel, J. *Psychopharmacology* 1978, 60, 13. Compounds 1a, 1d, 1l, 2b, 2e and 2o were tested and showed IC$_{50}$ values of less than 20 nM.

The 5-HT$_{1A}$ antagonistic activity of some of the compounds of the invention has been estimated in vitro at cloned 5-HT$_{1A}$ receptors, stably expressed in transfected HeLa cells (HA7). In this test, 5-HT$_{1A}$ antagonistic activity is estimated by measuring the ability of the compounds to antagonize the 5-HT induced inhibition of forskolin induced cAMP accumulation. The assay was performed as a modification of the method described by Pauwels, P. J. et al. *Biochem. Pharmacol.* 1993, 45, 375. Compounds 1a, 1d, 1l, 2b and 2e were tested and showed IC$_{50}$ values of less than 7000 nM.

Some of the compounds of the invention have also been tested for their in vivo effect on 5-HT$_{1A}$ receptors in the assay described by Sanchez. C. et al. *Eur. J. Pharmacol.* 1996, 315, pp 245. In this test, antagonistic effects of test compounds are determined by measuring the ability of the test compounds to inhibit 5-MeO-DMT induced 5-HT syndrome.

The compounds of the present invention possess valuable activity as serotonin re-uptake inhibitors and have antagonistic effect at 5-HT$_{1A}$ receptors. The compounds of the invention are therefore considered useful for the treatment of diseases and disorders responsive to the inhibition of serotonin re-uptake and antagonistic activity at 5-HT$_{1A}$ receptors. Diseases responsive to the inhibition of serotonin re-uptake are well-known in the art and include affective disorders, such as depression, psychosis, anxiety disorders including general anxiety disorder, panic disorder, obsessive compulsive disorder, etc.

As explained above, the antagonistic activity at 5-HT$_{1A}$ receptors of the compounds of the invention will counteract the negative feed back mechanism induced by the inhibition of serotonin reuptake and is thereby expected to improve the effect of the serotonin reuptake inhibiting activity of the compounds of the invention.

The compounds as claimed herein are therefore considered to be particularly useful as fast onset of action medicaments for the treatment of depression. The compounds may also be useful for the treatment of depressions which are non-responsive to currently available SSRIs.

Some of the compounds of the invention have also been found to have affinity to dopamine D$_3$ and D$_4$ receptors in the following two assays.

Inhibition of the Binding of $^3$H-YM-09151-2 to Human Dopamine D$_4$ Receptors

By this method, the inhibition by drugs of the binding of [$^3$H]YM-09151-2 (0.06 nM) to membranes of human cloned dopamine D$_{4.2}$ receptors expressed in CHO-cells is determined in vitro. Method modified from NEN Life Science Products, Inc., technical data certificate PC2533-10/96.

Inhibition of the Binding of [$^3$H]-Spiperone to Human D$_3$ Receptors

By this method, the inhibition by drugs of the binding [$^3$H]Spiperone (0.3 nM) to membranes of human cloned dopamine D3-receptors expressed in CHO-cells is determined in vitro. Method modified from R. G. MacKenzie et al. *Eur. J. Pharm.-Mol. Pharm. Sec.* 1994, 266, 79-85.

Some of the compounds of the invention have also been tested for their in vivo effect on 5-HT$_{1A}$ receptors in the assay described by Sanchez, C. et al. *Eur. J. Pharmacol.* 1996, 315, pp 245. In this test, antagonistic effects of test compounds are determined by measuring the ability of the test compounds to inhibit 5-MeO-DMT induced 5-HT syndrome.

Accordingly, as the compounds of the invention show affinities in the described tests, they are considered useful in the treatment of affective disorders, such as depression, generalised anxiety disorder, panic disorder, obsessive compulsive disorders, social phobia and eating disorders, and neurological disorders such as psychosis.

What is claimed is:

1. A compound represented by the formula I wherein
A represents O or S;
n is 2, 3, 4, 5, 6, 7, 8, 9 or 10;
m is 2;
W represents N;
Q represents N, C or CH;
$R^1$ represents hydrogen, $C_{1-6}$-alkyl, $C_{2-6}$-alkenyl, $C_{2-6}$-alkynyl, $C_{3-8}$-cycloalkyl-$C_{1-6}$-alkyl, aryl-$C_{1-6}$-alkyl or acyl;
$R^2$, $R^3$, $R^4$, $R^5$ and $R^6$ independently represent hydrogen, halogen, cyano, nitro, $C_{1-6}$-alkyl, $C_{1-6}$-alkoxy, $C_{1-6}$-alkylsulfanyl, $C_{1-6}$ alkylsulfonyl, hydroxy, hydroxy-$C_{1-6}$-alkyl, $C_{1-6}$-alkoxycarbonyl, acyl, $C_{3-8}$-cycloalkyl, $C_{3-8}$-cycloalkyl-$C_{1-6}$-alkyl, trifluoromethyl, trifluoromethoxy, NR$^{15}$R$^{16}$ wherein R$^{15}$ and R$^{16}$ independently represent hydrogen, $C_{1-6}$-alkyl, $C_{3-8}$-cycloalkyl or phenyl; or R$^{15}$ and R$^{16}$ together with the nitrogen to which they are attached form a pyrrolidine or piperidine;
$R^7$ and $R^{7\prime}$ independently represent hydrogen or $C_{1-6}$-alkyl;
$R^8$, $R^9$, $R^{10}$ and $R^{11}$ are each independently selected from hydrogen, halogen, nitro, cyano, trifluoromethyl, trifluoromethoxy, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, phenyl, thiophenyl, $C_{1-6}$-alkoxy, $C_{1-6}$-alkylsulfanyl, $C_{1-6}$-alkylsulfonyl, hydroxy, formyl, acyl, acylamino, aminocarbonyl, $C_{1-6}$-alkoxycarbonylamino, aminocarbonylamino, $C_{1-6}$-alkylaminocarbonylamino and di($C_{1-6}$-alkyl)amino-carbonylamino, NR$^{13}$R$^{14}$ wherein R$^{13}$ and R$^{14}$ independently represent hydrogen, $C_{1-6}$-alkyl, $C_{3-8}$-cycloalkyl or phenyl; or $R^{13}$ and $R^{14}$ together with the nitrogen to which they are attached form a pyrrolidine or piperidine; or an enantiomer or pharmaceutically acceptable acid addition salt thereof.

2. The compound according to claim 1, wherein n is 2, 3 or 4.

3. The compound according to claim 1, wherein $R^7$ and $R^{7'}$ are both hydrogen.

4. The compound according to claim 1, wherein $R^1$ is hydrogen.

5. The compound according to claim 1, wherein $R^2$, $R^3$, $R^4$, $R^5$ and $R^6$ represent hydrogen.

6. The compound according to claim 1, wherein $R^8$, $R^9$, $R^{10}$ and $R^{11}$ independently represent hydrogen, halogen, $C_{1-6}$-alkyl, $C_{3-8}$-cycloalkyl, CN, $CF_3$, $OCF_3$, $NH_2$, $NR^{13}R^{14}$ wherein $R^{13}$ and $R^{14}$ independently represent hydrogen, $C_{1-6}$-alkyl, $C_{3-8}$-cycloalkyl or phenyl; or $R^{13}$ and $R^{14}$ together with the nitrogen form a piperidine or pyrrolidine.

7. The compound according to claim 6, wherein $R^8$, $R^9$, $R^{10}$ and $R^{11}$ independently represent methyl, cyclopropyl, trifluoromethyl, cyano, chloro, bromo, piperidinyl, phenyl.

8. A compound selected from the group consisting of:
2-{2-[4-(1H-Indol-4-yl)piperazin-1-yl]ethylsulfanyl}-4,6-dimethylnicotinonitrile,
2-{2-[4-(1H-Indol-4-yl)piperazin-1-yl]ethylsulfanyl}-6-(thiophen-2-yl)-4-trifluoromethylnicotinonitrile,
2-{2-[4-(1H-Indol-4-yl)piperazin-1-yl]ethylsulfanyl}pyridine,
2-{2-[4-(1H-Indol-4-yl)piperazin-1-yl]ethylsulfanyl}-6-methylnicotinonitrile,
3-{2-[4-(1H-Indol-4-yl)piperazin-1-yl]ethoxy}-2-chloropyridine,
3-{2-[4-(1H-Indol-4-yl)piperazin-1-yl]ethoxy}-2-bromopyridine,
3-{2-[4-(1H-Indol-4-yl)piperazin-1-yl]ethoxy}-2-methylpyridine,
3-{2-[4-(1H-Indol-4-yl)piperazin-1-yl]ethoxy}-5-chloropyridine,
2-{4-[4-(1H-Indol-4-yl)piperazin-1-yl]butylsulfanyl}-5-trifluoromethylpyridine,
2-{4-[4-(1H-Indol-4-yl)piperazin-1-yl]butylsulfanyl}-4,6-dimethylnicotinonitrile,
2-{3-[4-(1H-Indol-4-yl)piperazin-1-yl]propylsulfanyl}-5-trifluoromethylpyridine,
2-{3-[4-(1H-Indol-4-yl)piperazin-1-yl]propylsulfanyl}-4,6-dimethylnicotinonitrile,
2-{2-[4-(1H-Indol-4-yl)piperazin-1-yl]ethylsulfanyl}-6-methylnicotinamide,
2-{2-[4-(1H-Indol-4-yl)piperazin-1-yl]ethylsulfanyl}nicotinonitrile,
2-{2-[4-(1H-Indol-4-yl)piperazin-1-yl]ethylsulfanyl}-4-methylpyridine,
2-{2-[4-(1H-Indol-4-yl)piperazin-1-yl]ethylsulfanyl}-4-methyl-6-(piperidin-1-yl)nicotinonitrile,
2-{2-[4-(1H-Indol-4-yl)piperazin-1-yl]ethylsulfanyl}-4-trifluoromethyl-6-cyclopropylnicotinonitrile,
2-{2-[4-(1H-Indol-4-yl)piperazin-1-yl]ethylsulfanyl}-3-methanesulfonyl-4-methyl-6-phenylpyridine,
2-{2-[4-(1H-Indol-4-yl)piperazin-1-yl]ethoxy}nicotinonitrile,
2-{2-[4-(1H-Indol-4-yl)piperazin-1-yl]ethoxy}-4-methylpyridine,
2-{2-[4-(1H-Indol-4-yl)piperazin-1-yl]ethoxy}-6-methylnicotinamide,
2-{2-[4-(1H-Indol-4-yl)piperazin-1-yl]ethoxy}-4-methyl-6-(piperidin-1-yl)nicotinonitrile,
2-{2-[4-(1H-Indol-4-yl)piperazin-1-yl]ethoxy}-4-trifluoromethyl-6-cyclopropylnicotinonitrile,
2-{2-[4-(1H-Indol-4-yl)piperazin-1-yl]ethoxy}-3-methanesulfonyl-4-methyl-6-phenylpyridine,
6-Chloro-2-{2-[4-(1H-indol-4-yl)piperazin-1-yl]ethylsulfanyl}-4-methylnicotinonitrile,
6-Chloro-5-fluoro-2-{2-[4-(1H-indol-4-yl)piperazin-1-yl]ethylsulfanyl}nicotinonitrile,
4,6-Dimethyl-2-{2-[4-(1H-indol-4-yl)piperazin-1-yl]ethylsulfanyl}pyrimidine,
5-Cyano-4-{2-[4-(1H-indol-4-yl)piperazin-1-yl]ethylsulfanyl}pyrimidine,
5-Cyano-4-{2-[4-(1H-indol-4-yl)piperazin-1-yl]ethylsulfanyl}-6-methylsulfanyl-2-phenylpyrimidine,
5-Ethyl-2-{2-[4-(1H-indol-4-yl)piperazin-1-yl]ethylsulfanyl}pyrimidine, and
2-{2-[4-(1H-Indol-4-yl)piperazin-1-yl]ethylsulfanyl}-4-trifluoromethylpyrimidine,
or a pharmaceutically acceptable acid addition salt thereof.

9. A pharmaceutical composition comprising at least one compound according to claim 1 or claim 8, in a therapeutically effective amount and in combination with one or more pharmaceutically acceptable carriers or diluents.

10. A method for the treatment of a disorder or disease of a living animal body selected from the group consisting of psychosis, general anxiety disorder, panic disorder, obsessive compulsive disorder, depression and social phobia comprising administering to such a living animal body a therapeutically effective amount of a compound according to claim 1 or claim 8.

11. The method according to claim 10 wherein said animal body is a human body.

12. The method according to claim 10 wherein the administered compound is a pharmaceutically acceptable addition salt.

13. The method of claim 10 wherein said disorder or disease is psychosis.

14. The method of claim 10 wherein said disorder or disease is depression.

15. The compound according to claim 1 wherein the compound is a pharmaceutically acceptable addition salt of said compound of formula I.

16. The compound according to claim 8 wherein the compound is a pharmaceutically acceptable addition salt of said compound of formula I.

17. The composition according to claim 9 wherein said at least one compound is a pharmaceutically acceptable addition salt.

* * * * *

UNITED STATES PATENT AND TRADEMARK OFFICE
CERTIFICATE OF CORRECTION

PATENT NO. : 7,342,015 B2
APPLICATION NO. : 10/482762
DATED : March 11, 2008
INVENTOR(S) : Mario Rottländer et al.

It is certified that error appears in the above-identified patent and that said Letters Patent is hereby corrected as shown below:

Column 4, lines 17-19, "In preferred embodiments of the invention, $R^8$, $R^9$, $R^{10}$ and $R^{11}$ independently represent hydrogen, halogen, $C_{1-6}$-alkyl, $C_{3-8}$-cycloalkyl, CN, $CF_3$, $OCF_3$, $NH_2$, $NR^{13}R^{14}$" should read -- In preferred embodiments of the invention, $R^8$, $R^9$, $R^{10}$ and $R^{11}$ independently represent hydrogen, halogen, $C_{1-6}$-alkyl, $C_{3-8}$-cycloalkyl, CN, $CF_3$, $OCF_3$, $NH_2$, or $NR^{13}R^{14}$; --.

Column 4, lines 26-27, "pyl, trifluoromethyl, cyano, chloro, bromo, piperidinyl, phenyl;" should read -- pyl, trifluoromethyl, cyano, chloro, bromo, piperidinyl, or phenyl; --.

Column 13, line 16 claim 6, "$C_{1-6}$-alkyl, $C_{3-8}$-cycloalkyl, CN, $CF_3$, $OCF_3$, $NH_2$, $NR^{13}R^{14}$" should read -- $C_{1-6}$-alkyl, $C_{3-8}$-cycloalkyl, CN, $CF_3$, $OCF_3$, $NH_2$, or $NR^{13}R^{14}$; --.

Column 13, lines 20-22 claim 7, "7. The compound according to claim 6, wherein $R^8$, $R^9$, $R^{10}$ and $R^{11}$ independently represent methyl, cyclopropyl, trifluoromethyl, cyano, chloro, bromo, piperidinyl, phenyl." should read -- 7. The compound according to claim 1, wherein $R^8$, $R^9$, $R^{10}$ and $R^{11}$ independently represent methyl, cyclopropyl, trifluoromethyl, cyano, chloro, bromo, piperidinyl, or phenyl. --.

Signed and Sealed this

Twenty-third Day of November, 2010

David J. Kappos
*Director of the United States Patent and Trademark Office*